(12) United States Patent
Kim

(10) Patent No.: US 10,174,287 B2
(45) Date of Patent: Jan. 8, 2019

(54) COMPOSITION FOR INDUCING DIRECT TRANSDIFFERENTIATION OF SOMATIC CELL INTO VASCULAR PROGENITOR CELL, AND USE THEREOF

(71) Applicant: UNIST(ULSAN NATIONAL INSTITUTE OF SCIENCE AND TECHNOLOGY), Ulsan (KR)

(72) Inventor: Jeong Beom Kim, Gimhae-si (KR)

(73) Assignee: UNIST(ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 0 days.

(21) Appl. No.: 15/120,171

(22) PCT Filed: Mar. 3, 2015

(86) PCT No.: PCT/KR2015/002039
§ 371 (c)(1),
(2) Date: Aug. 19, 2016

(87) PCT Pub. No.: WO2015/133792
PCT Pub. Date: Sep. 11, 2015

(65) Prior Publication Data
US 2017/0130204 A1    May 11, 2017

(30) Foreign Application Priority Data

Mar. 3, 2014  (KR) .................. 10-2014-0025095
Mar. 3, 2015  (KR) .................. 10-2015-0029725

(51) Int. Cl.
C12N 5/071    (2010.01)
A61K 35/44    (2015.01)
G01N 33/50    (2006.01)

(52) U.S. Cl.
CPC ............ *C12N 5/0692* (2013.01); *A61K 35/44* (2013.01); *G01N 33/5073* (2013.01); *C12N 2501/998* (2013.01); *C12N 2506/1307* (2013.01); *C12N 2510/00* (2013.01)

(58) Field of Classification Search
None
See application file for complete search history.

(56) References Cited

FOREIGN PATENT DOCUMENTS

WO    2012-006440    1/2012
WO    2013-181326    12/2013

OTHER PUBLICATIONS

Matsumoto (2001) "Downregulation and forced expression of EWS-Fli1 fusion gene results in changes in the expression of G1 regulatory genes" British Journal of Cancer, 84(6): 768-75.*
Asano, et al. (2013) "Fli1 Represses Transcription of the Human [alpha]2(I) Collagen Gene by Recruitment of the HDAC1/p300 Complex", PLOS one, 8(9): e74930 (11 pages).*
Moore, JC. The Role and Regulation of Etv2 in Zebrafish Vascular Development: A Dissertation. (2013). University of Massachusetts Medical School. GSBS Dissertations and Theses. Paper 672. DOI: 10.13028/M21K56. http://escholarship.umassmed.edu/gsbs_diss/ 672 (189 pages).*
Paar, et al. (2009) "Influence of vector design and host cell on the mechanism of recombination and emergence of mutant subpopulations of replicating retroviral vectors", BMC Molecular Biology, 10(8): doi:10.1186/1471-2199-10-8, pp. 1-14.*
Michael Ginsberg et al., "Efficient Direct Reprogramming of Mature Amniotic Cells into Endothelial Cells by ETS Factors and TGF~ Suppression", Cell, vol. 151(3), pp. 559-575, Oct. 26, 2012.
Kelly Larnmerts van Bueren et al., "Regulation of endothelial and hematopoietic development by the ETS transcription factor Etv2", Curr opin hematol, vol. 19(3), pp. 199-205, May 2012.
Ginsberg Michael et al: "Efficient Direct Reprogramming of Mature Amniotic Cells into Endothelial Cells by ETS Factors and TGF[beta] Suppression", Cell, vol. 151,No. 3, pp. 559-575, XP028952799, ISSN:0092-8674, DOI: 10.1016/J.CELL.2012.09.032.
Matthew B. Veldman et al:"Transdifferentiation of Fast Skeletal Muscle Into Functional Endothelium in Vivo by Transcription Factor Etv2", PLoS Biology, vol. 11, No. 6, Jun. 18, 2013 (Jun. 18, 2013), p. e1001590, XP55421855, DOI: 10.1371/journal.pbio. 1001590.
Ferris Cameron J et al: "Biofabrication: an overview of the approaches used for printing of living cells", Applied Microbiology and Biotechnology, Springer, DE, vol. 97, No. 10, Mar. 24, 2013 (Mar. 24, 2013), pp. 4243-4258, XP035328928, ISSN: 0175-7598, DOI: 10.1007/S00253-013-4853-6.

(Continued)

*Primary Examiner* — Robert M Kelly
(74) *Attorney, Agent, or Firm* — Lex IP Meister, PLLC

(57) ABSTRACT

The present invention relates to a composition for inducing direct transdifferentiation of a somatic cell into a vascular progenitor cell and a use thereof and, more specifically, to a composition for inducing direct transdifferentiation of a somatic cell into a vascular progenitor cell, a pharmaceutical composition for the prevention or treatment of ischemic vascular diseases, a cell therapeutic agent for the prevention or treatment of ischemic vascular diseases, a composition for screening a therapeutic drug for ischemic vascular diseases, a 3D printing biological material composition for the production of an artificial tissue for the treatment of ischemic vascular diseases, and a method for direct transdifferentiation of a somatic cell into a vascular progenitor cell. By producing a vascular progenitor cell by direct transdifferentiation of a somatic cell according to the present invention, it is possible to reduce the production period of the vascular progenitor cell and to avoid the formation of teratoma, which is a side effect of an induced pluripotent stem cell, thereby minimizing the side effects of a stem cell therapeutic agent.

4 Claims, 4 Drawing Sheets
(4 of 4 Drawing Sheet(s) Filed in Color)
Specification includes a Sequence Listing.

(56) References Cited

OTHER PUBLICATIONS

Hannah K. Wilson et al: "Concise Review: Tissue-Specific Microvascular Endothelial Cells Derived From Human Pluripotent Stem Cells : Stem Cell-Derived Tissue-Specific Endothelial Cells", Stem Cells., vol. 32, No. 12, Nov. 26, 2014, pp. 3037-3045, XP55382973, US ISSN: 1066-5099, DOI: 10.1002/stem.1797.
Van Pham Phuc et al: "Production of endothelial progenitor cells from skin fibroblasts by direct reprogramming for clinical usages", In Vitro Cellular & Developmental Biology. Animal, Springer US, New York, vol. 53, No. 3, Oct. 24, 2016 (Oct. 24, 2016), pp. 207-216, XP036187524, ISSN: 1071-2690, DOI: 10.1007/S11626-016-0106-1.
EPO, Extended European Search Report of European Patent Application No. 15758822.9, dated Nov. 16, 2017.

\* cited by examiner

SEQUENCE LISTING

<160> NUMBER OF SEQ ID NOS: 2

<210> SEQ ID NO 1
<211> LENGTH: 1510
<212> TYPE: DNA
<213> ORGANISM: Artificial Sequence
<220> FEATURE:
<223> OTHER INFORMATION: Synthetic (human ETV2 (ETS variant gene 2))

<400> SEQUENCE: 1

```
ttcctgttgc agataagccc agcttagccc agctgacccc agaccctctc ccctcactcc      60
ccccatgtcg caggatcgag accctgaggc agacagcccg ttcaccaagc ccccgcccc     120 gcccccatca ccccgtaaac ttctcccagc ctccgccctg ccctcaccca gcccgctgtt     180
ccccaagcct cgctccaagc ccacgccacc cctgcagcag ggcagcccca gaggccagca     240
cctatccccg aggctggggt cgaggctcgg ccccgcccct gcctctgcaa cttgagcctg     300
gctgcgaccc ctgctctgac gtctcggaaa attcccccctt gcccaggccc ttggggagg     360 gggtgcatgg tatgaaatgg ggctgagacc cccggctggg ggcagaggaa cccgccagag     420
aacattcaga aggccttcat cgcatccatg gacctgtgga actgggatga ggcatcccca     480
caggaagtgc ctccagggaa caagctggca gggcttgaag gagccaaatt aggcttctgt     540
ttccctgatc tggcactcca aggggacacg ccgacagcga cagcagagac atgctggaaa     600
ggtacaagct catccctggc aagcttccca cagctggact ggggctccgc gttactgcac     660
ccagaagttc catggggggc ggagcccgac tctcaggctc ttccgtggtc cggggactgg     720
acagacatgg cgtgcacagc ctgggactct tggagcggcg cctcgcagac cctgggcccc     780
gcccctctcg gcccgggccc catcccccgcc gccggctccg aaggcgccgc gggccagaac     840
tgcgtccccg tggcgggaga ggccacctcg tggtcgcgcg cccaggccgc cgggagcaac     900
accagctggg actgttctgt ggggcccgac ggcgatacct actggggcag tggcctggc      960 ggggagccgc gcacggactg taccatttcg tggggcgggc ccgcgggccc ggactgtacc    1020
acctcctgga acccggggct gcatgcgggt ggcaccacct ctttgaagcg gtaccagagc    1080
tcagctctca ccgtttgctc cgaaccgagc ccgcagtcgg accgtgccag tttggctcga    1140
tgccccaaaa ctaaccaccg aggtcccatt cagctgtggc agttcctcct ggagctgctc    1200
cacgacgggg cgcgtagcag ctgcatccgt tggactggca acagccgcga gttccagctg    1260
tgcgacccca aagaggtggc tcggctgtgg ggcgagcgca agagaaagcc gggcatgaat    1320
tacgagaagc tgagccgggg ccttcgctac tactatcgcc gcgacatcgt gcgcaagagc    1380 gggggcgaa agtacacgta ccgcttcggg ggccgcgtgc ccagcctagc ctatccggac    1440 tgtgcggag gcggacgggg agcagagaca caataaaaat tcccggtcaa acctcaaaaa    1500
aaaaaaaaaa                                                           1510
```

<210> SEQ ID NO 2
<211> LENGTH: 3995
<212> TYPE: DNA
<213> ORGANISM: Artificial Sequence
<220> FEATURE:
<223> OTHER INFORMATION: Synthetic (human FLI1 (Friend leukemia virus
      integration 1))

<400> SEQUENCE: 2

| | |
|---|---:|
| agagaagaga gaggagagct cgaggcgaga gagagagaga gagagagaga gagagagaga | 60 |
| gagagagaga gagagagata ggacttcctc cccgattcgc aaagtgaagt cacttcccaa | 120 |
| aattagctga aaaaaagtt tcatccggtt aactgtctct ttcgctccgc tacaacaaca | 180 |
| aacgtgcaca ggggagtgag ggcagggcgc tcgcagggg cacgcaggga gggcccaggg | 240 |
| cgccagggag gccgcgccgg gctaatccga aggggctgcg aggtcaggct gtaaccgggt | 300 |
| caatgtgtgg aatattgggg ggctcggctg cagacttggc caaatggacg ggactattaa | 360 |
| ggaggctctg tcggtggtga cgacgacca gtccctcttt gactcagcgt acggagcggc | 420 |
| agcccatctc cccaaggccg acatgactgc ctcggggagt cctgactacg gcagcccca | 480 |
| caagatcaac cccctcccac cacagcagga gtggatcaat cagccagtga gggtcaacgt | 540 |
| caagcgggag tatgaccaca tgaatggatc cagggagtct ccggtggact gcagcgttag | 600 |
| caaatgcagc aagctggtgg gcggaggcga gtccaacccc atgaactaca acagctatat | 660 |
| ggacgagaag aatggccccc ctcctcccaa catgaccacc aacgagagga gagtcatcgt | 720 |
| ccccgcagac cccacactgt ggacacagga gcatgtgagg caatggctgg agtgggccat | 780 |
| aaaggagtac agcttgatgg agatcgacac atcctttttc cagaacatgg atggcaagga | 840 |
| actgtgtaaa atgaacaagg aggacttcct ccgcgccacc ccctctacac acggaagt | 900 |
| gctgttgtca cacctcagtt acctcaggga agttcactg ctggcctata atacaacctc | 960 |
| ccacaccgac caatcctcac gattgagtgt caaagaagac ccttcttatg actcagtcag | 1020 |
| aagaggagct ggggcaata acatgaattc tggcctcaac aaaagtcctc cccttggagg | 1080 |
| ggcacaaacg atcagtaaga atacagagca acggccccag ccagatccgt atcagatcct | 1140 |
| gggcccgacc agcagtcgcc tagccaaccc tggaagcggg cagatccagc tgtggcaatt | 1200 |
| cctcctggag ctgctctccg acagcgccaa cgccagctgt atcacctggg aggggaccaa | 1260 |
| cggggagttc aaaatgacgg accccgatga ggtggccagg cgctggggcg agcggaaaag | 1320 |
| caagcccaac atgaattacg acaagctgag ccgggcctc cgttattact atgataaaaa | 1380 |
| cattatgacc aaagtgcacg gcaaaagata tgcttacaaa tttgacttcc acggcattgc | 1440 |
| ccaggctctg cagccacatc cgaccgagtc gtccatgtac aagtacccct ctgacatctc | 1500 |
| ctacatgcct tcctaccatg cccaccagca gaaggtgaac tttgtccctc ccatccatc | 1560 |
| ctccatgcct gtcacttcct ccagcttctt tggagccgca tcacaatact ggaccctcccc | 1620 |
| cacgggggga atctacccca accccaacgt ccccgccat cctaacaccc acgtgccttc | 1680 |
| acacttaggc agctactact agaagcttac tcatcagtgg ccttctagct gaagcccatc | 1740 |
| ctgcacactt actggatgct ttggactcaa caggacatat gtggccttga agggaagaca | 1800 |
| aaactggatg ttcttcttg ttggatagaa cctttgtatt tgttctttaa aaacattttt | 1860 |
| tttaatgttg gtaacttttg cttcctctac ctgaacaaag agatgaataa ttccatgggc | 1920 |
| cagtatgcca gtttgaattc tcagtctcct agcatcttgt gagttgcata ttaagattac | 1980 |
| tggaatggtt aagtcatggt tctgagaaag aagctgtacg ttttctttat gtttttatga | 2040 |

-continued

```
ccaaagcagt ttcttgtcaa tacacggggt tcagtatgac acagaatcat ggacttaacc    2100
cgtcatgttc tggtttgaga tttagtgaca aatagaggtg ggaagcttat aatctaattt    2160
taggaggacc aaattcagtg gatggcaact ggaacattga ttgtaaggcc agtgaagttt    2220
tcacccaact ggaatttgat ggaaagaagg tttgtgtgtt taagacgcca agggcattgc    2280
agaatccctc tcagtggaca gtatgcactc agctgaccac tctctctaga aatagtcaag    2340
atatgaacta agaaatttta atgcaaatac atacattcct gaaagacggg gaattaaatt    2400
actaattttt tttttttttt aaatgatgac agtggtccca gaacttggaa aagttgtagg    2460
gatttctaaa ctcaagcaga ttcgcaagtg ctgtgcgctt gtcagaccat cagaccaggg    2520
ccaaccaatc agaaggcaac ttactgtata aattatgcag agttattttc ctatatctca    2580
cagtattaaa aataaataat taaaaattaa gaataaataa acgagttgac ctcggtcaca    2640
aaagcagttt tactatcgaa tcaatcgctg ttatttttt taatgtaatt tgtacatctt    2700
ttttcaatct gtacatttgg gctgtctgta tgttttata gctggttttt aaaaagcata    2760
atatgcctat agctgaaaag gaaacagggc tgtttaagtc actgacttat gagaaagcaa    2820
agcactggta cagttattta acaggcatac acaagcaggg aaaagataat ccatttagat    2880
ctttaatgct ttggaaatgc gtgtaacagt actgcaataa tcacagctct gggaaaaaca    2940
acgaaacttt cccttgtgga gaggagggat tttcctgctc tatataagca acatattttt    3000
agacattaaa atatatataa ttttgcaggt aattgttgac tttttaact atattaagtg    3060
ttaagctgac aactgtcaaa gaagaccatg ttgtaaaata atttgactaa ataaatggtt    3120
ccttctctca gtgctgagga cagttttctt atttaccgcc cccgttaggt caagggttt    3180
tccctgggga actttcctat ttacttcttg cactatcaag aattttcga atgtacctac    3240
tgcagtacag cagaaggtaa aaaatcagtg tggttttca ttgttgttga tgatgtttgt    3300
agtgttttg tgtgtgttat ttaaatcttc ctccagccta aaagggtttt ataaaacagc    3360
agctaaggcc atggataaac ctgtatgtaa ggactggagc aaagcgagct ggtctatcca    3420
gactggtctg tgagatttaa ctctgcagcc tccctgggc acttcagacc cagacggcca    3480
ccttctgcca ctccagcaaa gaataagcgc cctgcttcct tcaggtctca gaccaggact    3540
ttatggctca tgcagatttt taaggtcatt tttcttccca aggaagaaac ttgcctccag    3600
ttccttcact gttaggtagc ttattttcat tttctctatt ttacaatgaa aagagtgaga    3660
cctgggaagt ccttgatttg caaggaatta gactcacagc attggtaacc ctagaacctt    3720
cttagggtaa cactaagtac cttctagaca acatgtctac ctaaatgaaa tgggatgtgt    3780
ttcggaacat ttgtctccag ttttttttta atcttgcacc ctgccattta aaaagatgtg    3840
taaagcacat attctcaaca tatgcacatt gatttataaa tcatatatac aaactgttac    3900
attattcttc atattagaaa acaaatacaa aatagaacat tttaaatggt gatataaaaa    3960
taaattgaaa ctgaaattct aaaaaaaaaa aaaaa                               3995
```

COMPOSITION FOR INDUCING DIRECT TRANSDIFFERENTIATION OF SOMATIC CELL INTO VASCULAR PROGENITOR CELL, AND USE THEREOF

TECHNICAL FIELD

The present invention relates to a composition for inducing the direct transdifferentiation of somatic cells into vascular progenitor cells, including at least one selected from the group consisting of a protein of each of direct transdifferentiation factors ETV2 and FLI1, a nucleic acid molecule encoding the protein, and a vector for expressing the protein by introducing the nucleic acid molecule encoding the protein, and to a method for the direct transdifferentiation of somatic cells into vascular progenitor cells and vascular cells using the above composition. In addition, the present invention relates to a pharmaceutical composition, a cell therapy agent, a drug screening composition, or a 3D printing biomaterial composition for the production of artificial tissue, each of which includes vascular progenitor cells and vascular cells induced by the above method for the direct transdifferentiation of somatic cells, thereby being used to prevent or treat ischemic vascular disease.

BACKGROUND ART

Blood vessel formation processes are largely classified into two types, namely vasculogenesis, in which angioblasts or vascular progenitor cells differentiate to form a primitive vascular network, and angiogenesis, in which new blood vessels are formed from existing vessels. During vasculogenesis, vascular progenitor cells differentiate into vascular endothelial cells and the like, yielding principal blood vessels. Vasculogenesis may include, depending on the pattern of differentiation of vascular progenitor cells, Type 1 vasculogenesis, in which vascular endothelial cells differentiate in situ, as in the production of blood vessels in the body, and Type 2 vasculogenesis, which occurs when vascular progenitor cells migrate over some significant distance and then differentiate, as in the formation of blood vessels in the endocardium or the cranial region. This acts as an important mechanism in various pathological states of inflammation, tumors and the like, as well as physiological states such as wound healing, ovulation, and pregnancy, including the fetal development process, and is thus under study.

Vascular injury causes a variety of ischemic diseases, and may be fundamentally treated through restoration of endogenous cells or transplantation of functional vascular cells for forming blood vessels. In this regard, treatment through the transplantation of functional vascular cells is problematic because effective methods of differentiating vascular cells are not readily available and because it is difficult to obtain large amounts of cells.

Also, methods of inducing the differentiation of embryonic stem cells (ESCs) and induced pluripotent stem cells into vascular cells have been proposed, but are disadvantageous because the efficiency of induction into cells of interest is low and there is the risk of activating tumor genes from the embryonic stem cells or pluripotent stem cells upon differentiation into specific cells. Furthermore, although induced pluripotent stem cells are able to avoid ethical issues associated with embryonic destruction and are resistant to immune system rejection when transplanted, they are undesirably liable to form teratoma, as in the embryonic stem cells.

Also, methods of preparing vascular progenitor cells from somatic cells through direct transdifferentiation have not yet been reported. In particular, the establishment of multipotency of vascular cells by direct transdifferentiation of somatic cells through transduction of ETV2 (ETS variant gene 2) or FLI1 (Friend leukemia virus integration 1) is not known.

DISCLOSURE

Technical Problem

Accordingly, an object of the present invention is to provide a composition for inducing the direct transdifferentiation of somatic cells into vascular progenitor cells, including, as an active ingredient, at least one protein selected from among ETV2 (ETS variant gene 2) and FLI1 (Friend leukemia virus integration 1), a nucleic acid molecule encoding the protein, or a vector having the nucleic acid molecule introduced thereto.

Another object of the present invention is to provide a pharmaceutical composition for the prevention or treatment of ischemic vascular disease, a cell therapy agent for the prevention or treatment of ischemic vascular disease, a drug screening composition for the treatment of ischemic vascular disease, or a 3D printing biomaterial composition for manufacturing artificial tissue for the treatment of ischemic vascular disease, each of which includes, as an active ingredient, at least one protein selected from among ETV2 (ETS variant gene 2) and FLI1 (Friend leukemia virus integration 1), a nucleic acid molecule encoding the protein, a vector having the nucleic acid molecule introduced thereto, or a vascular progenitor cell induced through direct transdifferentiation.

Still another object of the present invention is to provide a method for the direct transdifferentiation of somatic cells into vascular progenitor cells.

Technical Solution

In order to accomplish the above objects, the present invention provides a composition for inducing the direct transdifferentiation of a somatic cell into a vascular progenitor cell, including, as an active ingredient, at least one protein selected from among ETV2 (ETS variant gene 2) and FLI1 (Friend leukemia virus integration 1), a nucleic acid molecule encoding the protein, or a vector comprising the nucleic acid molecule.

In addition, the present invention provides a vascular progenitor cell induced through direct transdifferentiation by introducing at least one protein selected from among ETV2 (ETS variant gene 2) and FLI1 (Friend leukemia virus integration 1), a nucleic acid molecule encoding the protein, or a vector comprising the nucleic acid molecule, to a somatic cell.

In addition, the present invention provides a pharmaceutical composition for the prevention or treatment of ischemic vascular disease, including, as an active ingredient, at least one protein selected from among ETV2 (ETS variant gene 2) and FLI1 (Friend leukemia virus integration 1), a nucleic acid molecule encoding the protein, a vector comprising the nucleic acid molecule, or a vascular progenitor cell induced through direct transdifferentiation.

In addition, the present invention provides a cell therapy agent for the prevention or treatment of ischemic vascular disease, including, as an active ingredient, at least one protein selected from among ETV2 (ETS variant gene 2)

and FLI1 (Friend leukemia virus integration 1), a nucleic acid molecule encoding the protein, a vector comprising the nucleic acid molecule, or a vascular progenitor cell induced through direct transdifferentiation.

In addition, the present invention provides a drug screening composition for the treatment of ischemic vascular disease, including, as an active ingredient, at least one protein selected from among ETV2 (ETS variant gene 2) and FLI1 (Friend leukemia virus integration 1), a nucleic acid molecule encoding the protein, a vector comprising the nucleic acid molecule, or a vascular progenitor cell induced through direct transdifferentiation.

In addition, the present invention provides a 3D printing biomaterial composition for manufacturing artificial tissue for the treatment of ischemic vascular disease, including, as an active ingredient, at least one protein selected from among ETV2 (ETS variant gene 2) and FLI1 (Friend leukemia virus integration 1), a nucleic acid molecule encoding the protein, a vector comprising the nucleic acid molecule, or a vascular progenitor cell induced through direct transdifferentiation.

In addition, the present invention provides a method for direct transdifferentiation of a somatic cell into a vascular progenitor cell, including introducing at least one protein selected from among ETV2 (ETS variant gene 2) and FLI1 (Friend leukemia virus integration 1), a nucleic acid molecule encoding the protein, or a vector comprising the nucleic acid molecule, to the somatic cell.

Advantageous Effects

According to the present invention, vascular progenitor cells can be prepared from somatic cells through direct transdifferentiation, thereby decreasing the period of time required to prepare vascular progenitor cells and avoiding the formation of teratoma, which is a dysfunction of induced pluripotent stem cells, ultimately minimizing the side effects of stem cell therapy agents.

DESCRIPTION OF DRAWINGS

The file of this patent contains at least one drawing executed in color. Copies of this patent with color drawing (s) will be provided by the Patent and Trademark Office upon request and payment of the necessary fee.

BEST MODE

Figure 1:
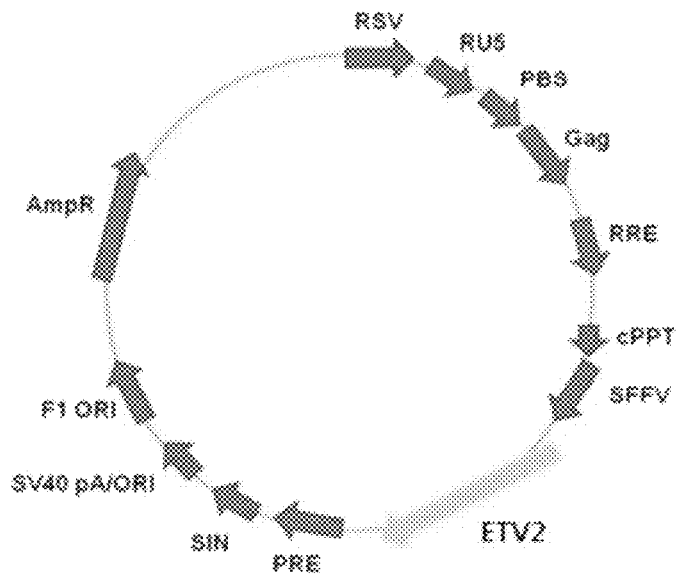
FIG. 1 illustrates the cleavage map of Lentivirus encoding complementary DNA of ETV2.
Figure 2:
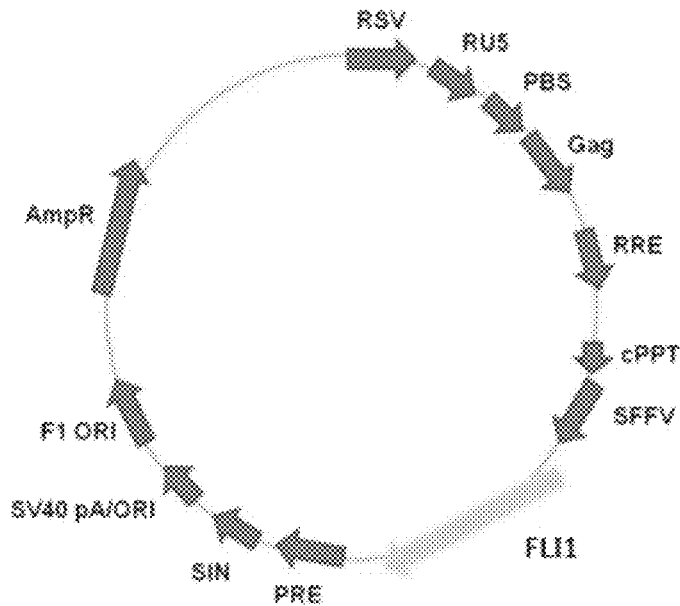
FIG. 2 illustrates the cleavage map of Lentivirus encoding complementary DNA of FLI1.

The present invention addresses a composition for inducing the direct transdifferentiation of somatic cells into vascular progenitor cells, including, as an active ingredient, at least one protein selected from among ETV2 (ETS variant gene 2) and FLI1 (Friend leukemia virus integration 1), a nucleic acid molecule encoding the protein, or a vector having the nucleic acid molecule introduced thereto.

In the present invention, ETV2 (ETS variant gene 2) is a member of the ETS (E26 transformation-specific or E-twenty-six) family, and is registered with NCBI Registration No. NM_014209.3 (SEQ ID NO: 1). The ETS factor is known to be associated with embryonic blood vessel development. In particular, ETV2 is known to perform an essential regulatory function in vascular endothelial differentiation, but the function thereof for inducing the direct transdifferentiation of somatic cells into vascular progenitor cells is not known at all.

Also, FLI1 (Friend leukemia virus integration 1) is a member of the ETS family, and is registered with NCBI Registration No. NM_002017.4 (SEQ ID NO: 1). It is known to inhibit the differentiation of red blood cells through constitutive activation in the erythroblasts. In particular, the function of FLI1 for inducing the direct transdifferentiation into vascular progenitor cells is not known at all, like ETV2.

In the present invention, ETV2, FLI1, or a combination thereof may be provided in the form of a protein or a nucleic acid encoding the protein, and the protein may include any ETV2 or FLI1 protein derived from humans or animals, such as mice, horses, sheep, pigs, goats, camels, antelopes, and dogs. Furthermore, the ETV2 or FLI1 protein used in the present invention includes not only a protein having a wild-type amino acid sequence but also a protein variant of the ETV2 or FLI1 protein.

The term "protein variant" refers to a protein, at least one amino acid residue of which differs from the native amino acid sequence of an ETV2 or FLI1 protein, resulting from deletion, insertion, non-conservative or conservative substitution, or combinations thereof. The variant may be a functional equivalent that shows the same biological activity as a native protein, may be a variant in which the physical and chemical properties of a protein are modified as necessary, or may be a variant the structural stability of which is increased under certain physical or chemical conditions, or the physiological activity of which is increased.

In the present invention, a nucleic acid encoding ETV2 or FLI1 may have a base sequence encoding the wild-type or variant-type ETV2 or FLI1 protein, and may be mutated by subjecting at least one base to substitution, deletion, insertion, or combinations thereof. Also, it may be prepared via extraction from nature or using a chemical synthesis method. The nucleic acid having the base sequence encoding the ETV2 or FLI1 protein may be a single chain or a double chain, and may be a DNA molecule (genomic DNA, cDNA) or an RNA molecule.

In the present invention, the vector may include a signal sequence or a reader sequence for membrane targeting or secretion, in addition to an expression regulatory element, such as a promoter, an operator, an initiation codon, a termination codon, a polyadenylation signal, or an enhancer, and may be variously manufactured so as to be adapted for some purpose. The promoter of the vector may be constructive or inductive. Furthermore, the expression vector includes a selective marker for selecting a host cell containing the vector, and a replicable expression vector includes a replication origin. The vector may be self-replicating, or may be integrated into the host DNA.

The vector includes a plasmid vector, a cosmid vector, a viral vector, and an episomal vector. Preferably useful is a viral vector. An example of the viral vector may include, but is not limited to, a vector derived from Retrovirus, for example, HIV (Human Immunodeficiency Virus), MLV (Murine Leukemia Virus), ASLV (Avian Sarcoma/Leukosis), SNV (Spleen Necrosis Virus), RSV (Rous Sarcoma Virus), MMTV (Mouse Mammary Tumor Virus), Adenovirus, Adeno-associated virus, Herpes simplex virus, etc. In particular, the vector is used to increase the efficiency of direct transdifferentiation. Any vector that exhibits the effects of the present invention may be used, so long as it causes genes associated with cells to be converted to be over-expressed in typical somatic cells. Specifically, the vector may be exemplified by a lentiviral vector that expresses ETV2 or FLI1, and particularly an SF-based lentiviral vector as an SFFV promoter.

Also, the nucleic acid encoding the ETV2 or FLI1 protein may be transferred or introduced into cells using any process known in the art, for example, using a vector-type naked DNA, or using a liposome, cationic polymer, etc.

The liposome is a phospholipid membrane obtained through mixing with cationic phospholipids such as DOTMA or DOTAP for gene delivery. When a cationic liposome and an anionic nucleic acid are mixed at a predetermined ratio, a nucleic acid-liposome complex may be formed, and may thereby be introduced into the cells.

Specifically in the present invention, the nucleic acid molecule encoding the ETV2 or FLI1 protein is contained in a viral vector, and thereby the viral vector, which includes the nucleic acid encoding the ETV2 or FLI1 protein, may be introduced into somatic cells together with a packaging-defective helper plasmid. Examples of the virus may include, but are not limited to, Retrovirus, Adenovirus, Adeno-associated virus, Herpes simplex virus, etc.

As used herein, the term "somatic cell" refers to any cell other than a germ cell. Examples of somatic cells may include fibroblasts, muscle cells, nerve cells, gastric mucosal cells, goblet cells, G cells, pericytes, astrocytes, B cells, blood cells, epithelial cells, neural stem cells, hematopoietic stem cells, mesenchymal stem cells, and cord blood stem cells. However, direct transdifferentiation may be applied regardless of the specific kind of tissue cell, so long as it starts from somatic cells, and the present invention is not limited to the above examples of somatic cells. In an embodiment of the present invention, direct transdifferentiation is induced using fibroblasts.

As used herein, the term "vascular progenitor cell" refers to a progenitor cell having the ability to differentiate into a vascular endothelial cell, a vascular smooth muscle cell, a pericyte, or a vascular cell, which is a constituent of the blood vessel in vivo. Also, in the present invention, "iVPC" designates an induced vascular progenitor cell, for example, an induced vascular progenitor cell obtained from a somatic cell through direct differentiation according to the method of the present invention.

In addition, the present invention addresses a pharmaceutical composition for the prevention or treatment of ischemic vascular disease, including, as an active ingredient, at least one protein selected from among ETV2 (ETS variant gene 2) and FLI1 (Friend leukemia virus integration 1), a nucleic acid molecule encoding the protein, a vector having the nucleic acid molecule introduced thereto, or a vascular progenitor cell induced through direct transdifferentiation.

In addition, the present invention addresses a cell therapy agent for the prevention or treatment of ischemic vascular disease, including, as an active ingredient, at least one protein selected from among ETV2 (ETS variant gene 2) and FLI1 (Friend leukemia virus integration 1), a nucleic acid molecule encoding the protein, a vector having the nucleic acid molecule introduced thereto, or a vascular progenitor cell induced through direct transdifferentiation.

In addition, the present invention addresses a drug screening composition for the treatment of ischemic vascular disease, including, as an active ingredient, at least one protein selected from among ETV2 (ETS variant gene 2) and FLI1 (Friend leukemia virus integration 1), a nucleic acid molecule encoding the protein, a vector having the nucleic acid molecule introduced thereto, or a vascular progenitor cell induced through direct transdifferentiation.

Ischemic vascular disease refers to any disease that causes blood flow disorder due to blood vessel impairment by external or internal causes, and is not limited to generation at specific portions in vivo. Specific examples of the ischemic vascular disease may include, but are not limited to, cerebrovascular disease, cardiovascular disease, limb ischemia, peripheral vascular disease, and ischemic muscle necrosis. More specifically, the cerebrovascular disease may be cerebral infarction, stroke, or brain hemorrhage, and may include any blood flow disorder attributable to cerebrovascular damage, but the present invention is not limited to the examples of the above disease. Also, the cardiovascular disease may be arteriosclerosis, ischemic reperfusion injury, restenosis, arterial inflammation, vascular wall remodeling, ventricular remodeling, rapid ventricular pacing, coronary micro embolism, tachycardia, bradycardia, pressure overload, coronary artery ligation, arrhythmias, stroke, angina, myocardial infarction, heart failure, or hypertension, but may include any blood flow disorder attributable to cardiovascular damage, and the present invention is not limited to the examples of the above disease.

As used herein, the term "cell therapy agent" refers to a medicine (US FDA-regulated) used for the purpose of treatment, diagnosis or prevention of diseases with cells and tissues manufactured through culturing and specialized tasks after separation from human beings, especially a medicine used for the purpose of treatment, diagnosis or prevention of diseases by proliferating or screening autologous, allogeneic or xenogeneic living cells in vitro or otherwise changing the biological characteristics of cells in order to restore the functions of cells or tissues.

In addition, the present invention addresses a 3D printing biomaterial composition for manufacturing artificial tissue for the treatment of ischemic vascular disease, including, as an active ingredient, at least one protein selected from among ETV2 (ETS variant gene 2) and FLI1 (Friend leukemia virus integration 1), a nucleic acid molecule encoding the protein, a vector having the nucleic acid molecule introduced thereto, or a vascular progenitor cell induced through direct transdifferentiation.

In addition, the present invention addresses a method for the direct transdifferentiation of somatic cells into vascular progenitor cells, including introducing somatic cells with at least one protein selected from among ETV2 (ETS variant gene 2) and FLI1 (Friend leukemia virus integration 1), a nucleic acid molecule encoding the protein, or a vector having the nucleic acid molecule introduced thereto.

More specifically, the method includes: culturing somatic cells in a culture medium, transducing the cultured somatic cells with a vector containing ETV2, FLI1 or combined genes thereof, and culturing the infected somatic cells under culture conditions for inducing direct transdifferentiation.

The culture medium used for culturing the somatic cells includes any medium typically useful in the culture not only of somatic cells but also of stem cells and progenitor cells in the art. The culture medium usually contains a carbon source, a nitrogen source, and small amounts of elements. In a specific embodiment of the present invention, transduced fibroblasts are cultured in a culture medium supplemented with protamine sulfate (Sigma), but elements necessary for culturing the cells may be contained without limitation, in addition to the protamine sulfate.

Also, the culture conditions for inducing the direct transdifferentiation of somatic cells may include any culture medium typically used to induce direct transdifferentiation of somatic cells in the art. In a specific embodiment of the present invention, useful is a culture medium for growing vascular progenitor cells, comprising 10% PBS-containing minimal essential medium (MEM), 2 mM L-glutamine, β-mercaptoethanol, penicillin/streptomycin, and 10 ng/ml $VEGF_{165}$.

In the present invention, the vascular progenitor cells induced through direct transdifferentiation are associated with existing vascular differentiation and related vascular cell proliferation to thus aid new blood vessel formation, and may increase both the number and density of vascular cells, thereby exhibiting superior therapeutic effects on ischemic disease.

Mode for Invention

A better understanding of the present invention may be obtained through the following examples, which are set forth to illustrate, but are not to be construed as limiting the scope of the present invention. The examples of the present invention are provided to fully describe the present invention to those having ordinary knowledge in the art to which the present invention pertains.

Example 1. Preparation of Induced Vascular Progenitor Cells (iVPCs)

Dermal fibroblasts were cultured in a fibroblast medium (10% FBS-containing DMEM high glucose, 2 mM L-glutamine, 1×MEM nonessential amino acid, β-mercaptoethanol, 1× penicillin/streptomycin).

293 cells were infected with an SFFV promoter, that is, an SF-based lentiviral vector encoding complementary DNA of ETV2 and FLI1, and with a packaging-defective helper plasmid using a Fugene 6 transfection reagent (Roche). After 48 hr, a viral supernatant was obtained according to the method disclosed in Zaehres, H. & Daley, G. Q., (2006), Methods Enzymol 420, 49-64.

The dermal fibroblasts were aliquoted at a density of $1 \times 10^4$ cells into a 0.1% gelatin-coated 6-well plate and cultured for 24 hr, together with the viral supernatant that contained ETV2 and FLI1 (1:1) and was supplemented with 6 μg/ml protamine sulfate (Sigma). The transduction efficiency was calculated using SF-GFP control virus.

Two days after injection, the cells were aliquoted again into a new fibroblast medium, and the medium was replaced with a vascular progenitor cell growth medium (10% FBS-containing minimal essential medium (MEM, Sigma), 2 mM L-glutamine, β-mercaptoethanol, penicillin/streptomycin, 10 ng/ml $VEGF_{165}$ (Peprotech)). Thereafter, the medium was replaced with a new one at an interval of three days, and the colony was physically separated for proliferation.

Example 2. Expression of ETV2 and FLI1 Using RT-PCR and Phase-Contrast Microscopy Five days after infection, the expression of ETV2 and FLI1 was observed using RT-PCR.

Specifically, total RNA was extracted from each cell using an RNeasy kit (Qiagen), five days after the infection, and cDNA was synthesized using Omniscript RT (Qiagen). PCT was performed using a TaQ DNA polymerase recombinant (Invitrogen).

Figure 3:
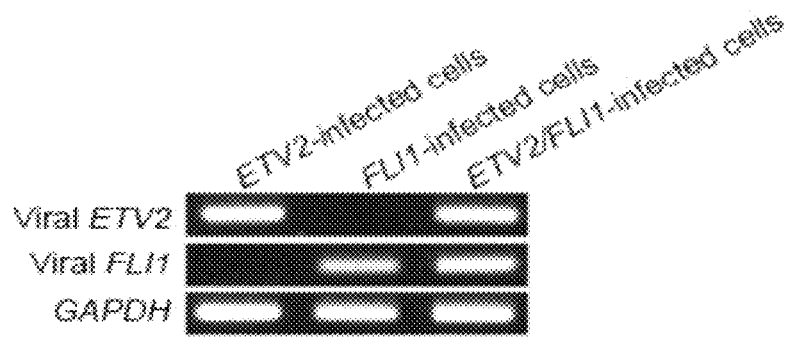
FIG. 3 illustrates the RT-PCR results of the expression of ETV2 and FLI1, 5 days after infection.

After RT-PCR, expression was confirmed through loading on agarose gel, using GAPDH as a control (FIG. 3).

Figure 4:
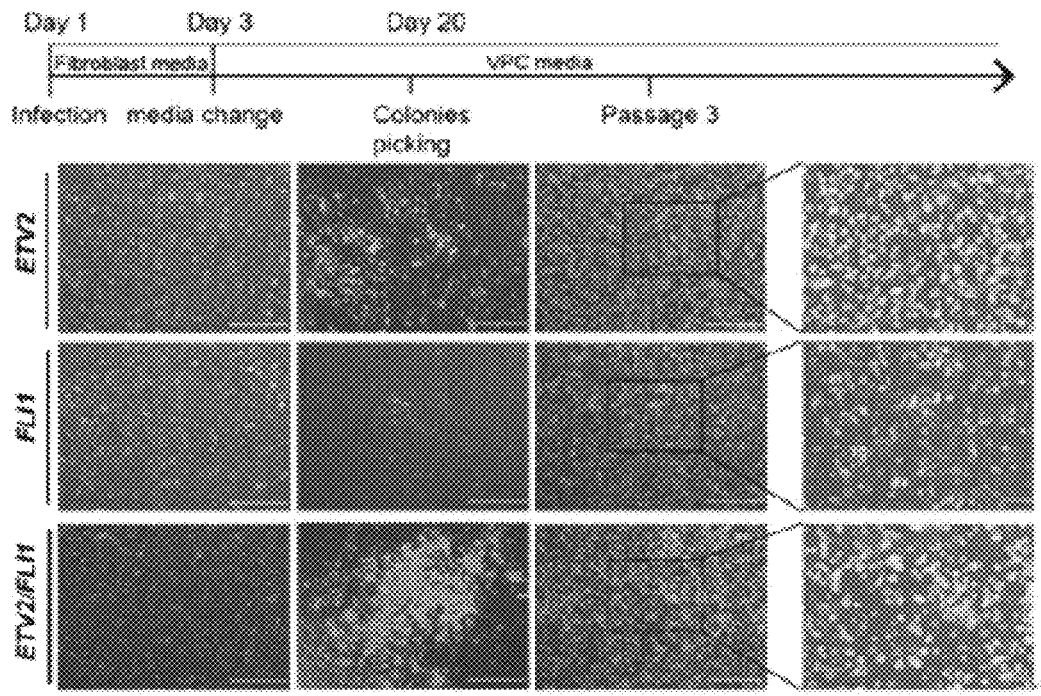
FIG. 4 illustrates phase-contrast images over time of vascular progenitor cells induced by being transformed with ETV2, FLI1 or ETV2/FLI1.

As illustrated in FIG. 4, using phase-contrast microscopy, colonies began to appear in the cell populations infected with ETV2 and ETV2/FLI1 within 10 to 11 days after the infection, and the number of colonies increased over time.

The present inventors observed colonies in the cell populations infected with FLI1 within 30 days after the infection. In order to proliferate the colonies, the cell populations were physically separated and cultured in a gelatin-coated dish.

Example 3. In Vitro Analysis of Vascular Progenitor Cells Using Immunocytochemistry In order to perform immunocytochemistry, the cells were immobilized for 10 min in 4% para-formaldehyde and treated with 0.1% Triton X-100 for 10 min so as to be permeable. The cells were cultured for 30 min in a 4% FBS/PBS blocking solution and then reacted for 1 hr with a primary antibody diluted with the blocking solution at room temperature. The primary antibody used was as follows: vWF (1:400, Abcam), CD31 (1:200, Chemicon) and α-SMA (1:200, Abcam).

After reaction with the primary antibody, the cells were washed three times with 0.05% PBST (tween20/PBS). Thereafter, a secondary fluorescent antibody was diluted with PBS and then reacted with the cells for 1 hr (Alexa Fluor 488 and 568; 1:1000, Molecular Probes). The cells were washed three times with 0.05% PBST, and the nuclei were counterstained for 15 sec using Hoechst 33342 (Thermo Scientific). After the staining, the cells were observed using an Olympus Cell^TIRF (UOBC center, UNIST) microscope.

Figure 5:
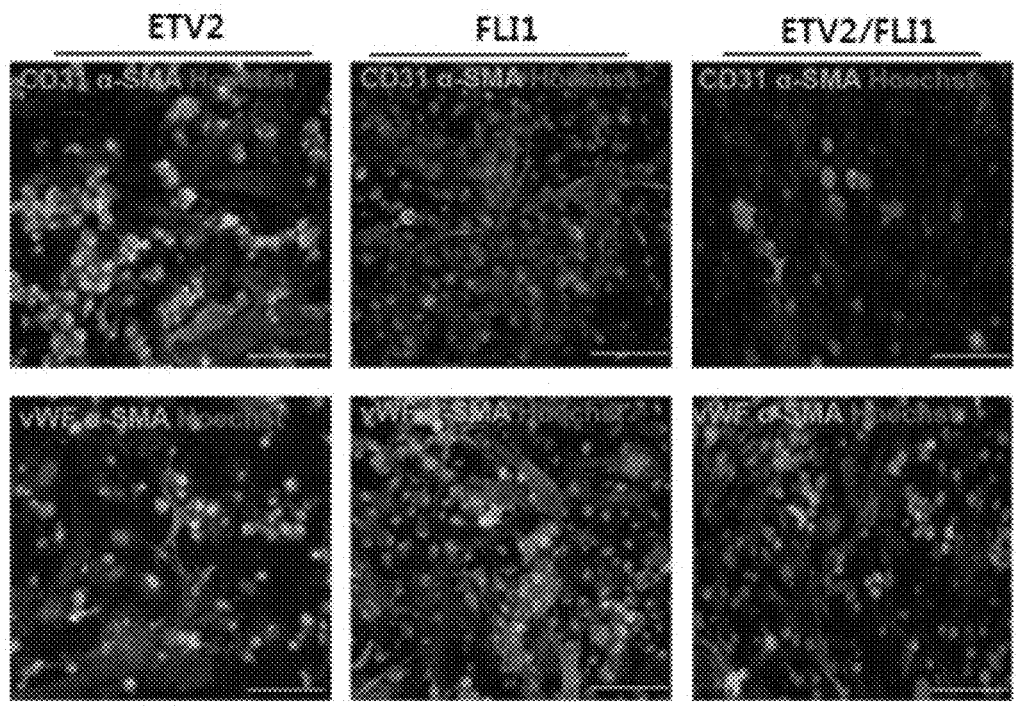
FIG. 5 is of immunofluorescence images illustrating the expression of vWF, α-SMA and CD31 as differentiation markers of induced vascular progenitor cells.

The vascular progenitor cells had properties such that they were capable of differentiation into vascular endothelial cells and smooth muscle cells, and CD31 and vWF were used as markers for the vascular endothelial cells, and α-SMA was used as a marker for the smooth muscle cells. Through immunocytochemical analysis, induced vascular progenitor cells (iVPCs) obtained through transformation by each of ETV2, FLI1 and ETV2/FLI1 were confirmed (FIG. 5).

Example 4. Effects of Induced Vascular Progenitor Cells on Treatment of Ischemic Disease In the ischemic limb model, whether induced vascular progenitor cells (induced-VPCs, iVPCs), obtained through transformation with ETV2, FLI1 and ETV2/FLI1, were effective at restoring blood flow was evaluated. To this end, the induced vascular progenitor cells were transplanted into the model. After a predetermined period of time, the blood flow was measured.

Specifically, thymus-free nude mice (male, 8 to 10-week-old, weight 17 to 22 g) were paralyzed with 160 mg/kg of pentobarbital for incision of the femoral artery and laser Doppler perfusion imaging. The femoral artery was incised to the distal point at which it is divided into the saphenous vein and the popliteal vein from the proximal tissue as branches of the external iliac artery. After arterial ligation, the mice were divided into the following test groups: ETV2, FLI1, and ETV2/FLI1 iVPC and a control (HBSS; saline injection) (n=8 per group).

Before the transplantation, the cells were labeled with CM-Dil (Invitrogen). Thereafter, four points of the gracilis muscle in the central thigh of each mouse were intramuscularly injected with 1×10⁶ cells (80 ↑L) or HBSS. 7, 14 and 28 days after transplantation of the cells into ischemic and normal limbs, as well as on the day of transplantation, measurement was performed using a laser Doppler perfusion imaging (LDPI) analyzer (Moor instruments, Devon, UK) (FIG. 6).

Figure 7:
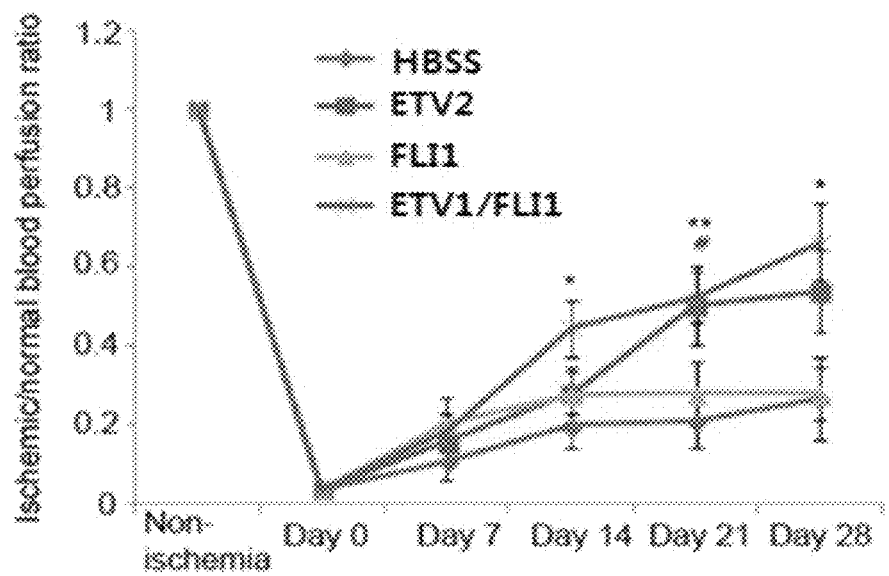
FIG. 7 illustrates the ischemic/nonischemic limb blood flow ratio, as represented by LDPI index, after transplantation of induced vascular progenitor cells into mice.

The blood flows of the ischemic and nonischemic limbs were calculated on the basis of colored histogram pixels. The red and the blue indicated high blood flow and low blood flow, respectively. The blood flow was represented by the LDPI index, corresponding to the ischemic/nonischemic limb blood flow ratio. In FIG. 7, the ratio before surgery, 1, indicates the same blood flow in two limbs.

Figure 6:
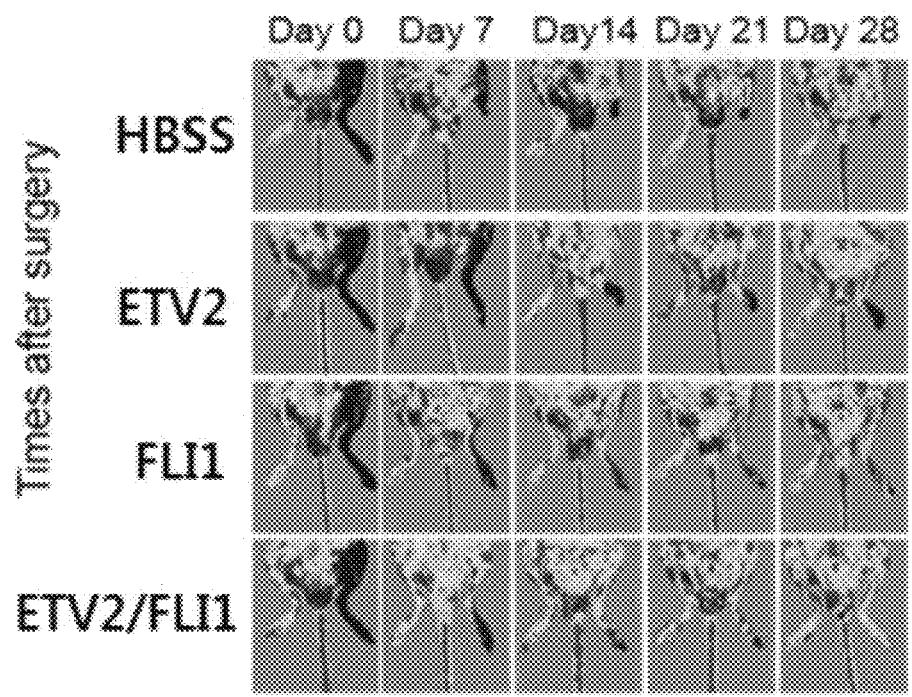
FIG. 6 illustrates blood flow over time, calculated on the basis of colored histogram pixels, after transplantation of induced vascular progenitor cells into mice.

With regard to the measurement results, as illustrated in FIGS. 6 and 7, all of the transplanted iVPC groups exhibited the restoration of blood flow in the ischemic limb model. In particular, the ETV2/FLI1 group manifested significantly increased blood flow restoration compared to the control.

The invention claimed is:

1. A method of inducing a direct transdifferentiation of a somatic cell into a vascular progenitor cell, comprising
   introducing one protein selected from the group consisting of ETV2 (ETS variant gene 2), and a combination of FLI1 (Friend leukemia virus integration 1) and ETV2,
   a nucleic acid molecule encoding the protein selected from the group consisting of ETV2, and a combination of FLI1 and ETV2, or
   a vector comprising the nucleic acid molecule, to a somatic cell, and
   wherein a vascular progenitor cell is formed directly from the somatic cell,
   wherein the somatic cell is a cell selected from the group consisting of a fibroblast, a muscle cell, a nerve cells, a gastric mucosal cell, a goblet cells, a G cells, a pericyte, an astrocyte, a B cell, a blood cell, an epithelial cell, a neural stem cell, a hematopoietic stem cell, a cord blood stem cell, and a mesenchymal stem cell.

2. The method of claim 1, wherein the vector is at least one selected from the group consisting of a plasmid vector, a cosmid vector, a viral vector, and an episomal vector.

3. The method of claim 2, wherein the viral vector is at least one selected from the group consisting of a retrovirus vector, an adenovirus vector, an adeno-associated virus, and a Herpes simplex virus vector.

4. The method of claim 3, wherein the retrovirus vector is at least one selected from the group consisting of a lentivirus vector, a HIV (Human Immunodeficiency Virus) vector, a MLV (Murine Leukemia Virus) vector, an ASLV (Avian Sarcoma/Leukosis) vector, a SNV (Spleen Necrosis Virus) vector, a RSV (Rous Sarcoma Virus) vector, and a MMTV (Mouse Mammary Tumor Virus) vector.

* * * * *